(12) United States Patent
Weitzel et al.

(10) Patent No.: US 7,318,804 B2
(45) Date of Patent: Jan. 15, 2008

(54) METHODS AND SYSTEMS FOR MEASURING MECHANICAL PROPERTY OF A VASCULAR WALL AND METHOD AND SYSTEM FOR DETERMINING HEALTH OF A VASCULAR STRUCTURE

(75) Inventors: William F. Weitzel, Ypsilanti, MI (US); Kang Kim, Ann Arbor, MI (US); Matthew O'Donnell, Ann Arbor, MI (US); Jonathan M. Rubin, Scio Township, MI (US); Hua Xie, Ann Arbor, MI (US); Xunchang Chen, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 198 days.

(21) Appl. No.: 10/731,302

(22) Filed: Dec. 9, 2003

(65) Prior Publication Data

US 2005/0124892 A1    Jun. 9, 2005

(51) Int. Cl.
*A61B 8/00* (2006.01)
(52) U.S. Cl. ..................... 600/438; 600/443
(58) Field of Classification Search ........ 600/437–438, 600/442–447, 454–456, 466–467, 500–501, 600/561–587; 73/573–575, 5
See application file for complete search history.

(56) References Cited

U.S. PATENT DOCUMENTS 5,265,612 A * 11/1993 Sarvazyan et al. .......... 600/471
5,524,636 A * 6/1996 Sarvazyan et al. .......... 600/587
6,165,128 A * 12/2000 Cespedes et al. ........... 600/463

OTHER PUBLICATIONS de Korte, C.L. et al "Characterization of Plaque Components and Vulnerability with Intravascular Ultrasound Elastography", Phys. Med. Biol. 45 (2000) 1465-1475.*
Bank, A.J., et al., "In Vivo Human Brachial Artery Elastic Mechanics Effects of Smooth Muscle Relaxation," 1999; Circulation 100: pp. 41-47.
Bergel, D.H., "The Static Elastic Properties of the Arterial Wall," J. Physiol., 1961; 156: pp. 445-457.

(Continued)

*Primary Examiner*—Francis J. Jaworski
(74) *Attorney, Agent, or Firm*—Brooks Kushman P.C.

(57) ABSTRACT

Methods and systems for measuring mechanical property of a vascular wall and a method and system for determining health of a vascular structure are provided wherein local deformation of a vessel wall resulting from physiologic pressures with altered transmural forces is measured. A non-invasive free-hand ultrasound scanning-procedure was performed to apply external force, comparable to the force generated in measuring a subject's blood pressure, to achieve higher strains by equalizing the internal arterial baseline pressure. When the applied pressure matched the internal baseline diastolic pressure, strain and strain rate increased by a factor of 10 over a cardiac cycle. Radial arterial strain was assessed in the vessel wall over the entire deformation procedure using a phase-sensitive, two-dimensional speckle-tracking algorithm. An elastic modulus reconstruction procedure was developed to estimate the non-linear elastic properties of the vascular wall.

40 Claims, 6 Drawing Sheets

OTHER PUBLICATIONS

Bilato, C., et al., "Atherosclerosis and Vascular Biology of Aging," Aging (Milano) 1996; 8: pp. 221-234.

Bonnefous, O., et al., "Non Invasive Echographic Techniques for Arterial Wall Characterization," IEEE Ultrasonic Symposium, 1996: pp. 1059-1064.

Blacher, J., et al., "Carotid Arterial Stiffness as a Predictor of Cardiovascular and All-Cause Mortality in End-Stage Renal Disease," Hypertension, 1998; 32: pp. 570-574.

Blacher, J., et al., "Impact of Aortic Stiffness on Survival in End-Stage Renal Disease," Circulation 1999; 99: pp. 2434-2439.

Bonnefous, O., et al., "New TDI Developments for Vascular and Cardiac Applications," IEEE Ultrasonic Symposium, 2000: pp. 1285-1290.

Bruel, A., et al., "Changes in Biomechanical Properties, Composition of Collagen and Elastin, and Advanced Glycation Endproducts of the Rat Aorta in Relation to Age," Atherosclerosis 1996; 127: pp. 155-165.

Duprez, D., et al., "Relationship Between Periventricular or Deep White Matter Lesions and Arterial Elasticity Indices in Very Old People," Age and Ageing, 2001; 30: pp. 325-330.

Eriksson, A., et al., "Arterial Pulse Wave Velocity with Tissue Doppler Imaging," Ultrasound in Med. & Biol., 2002; vol. 28, No. 5: pp. 571-580.

Gaury, G., "Function-Structure Relationship of Elastic Arteries in Evolution: From Microfibrils to Elastin and Elastic Fibres," Pathol. Biol., 2001; 49: pp. 310-325.

Y.C. Fung, "Biomechanics: Mechanical Properties of Living Tissues," 2nd Ed., Spring-Verlag, 1993: pp. 321-391.

Guerin, G., et al., "Arterial Stiffening and Vascular Calcifications in End-Stage Renal Disease," Nephro Dial Transplantation, 2000; 15: pp. 1014-1021.

Hardung, V., "Propagation of Pulse Waves in Visco-Elastic Tubing," American Physiological Society, Handbook of Physiology, Section 2, Circulation, 1962, vol. 1, eds., Hamilton, W.F. and Dow, p. 107-135.

Kaiser, D.R., et al., "Brachial Artery Elastic Mechanics in Patients with Heart Failure," 2001; Hypertension 38: pp. 1440-1445.

Konner, K., et al., "The Arteriovenous Fistula," J. Am. Soc. Nephrol., 2003; 14(6): pp. 1669-1680.

Langewouters, G.J., et al., "The Static Elastic Properties of 45 Human Thoracic and 20 Abdominal Aortas In Vitro and the Parameters of a New Model," J. Biomech., 1984; 17-425-435.

Lubinski, M.A., et al., "Speckle Tracking Methods for Ultrasonic Elasticity Imaging Using Short Time Correlation," IEEE Trans. Ultrason., Ferroelect., Freq. Contr., 1999, vol. 46, pp. 82-96.

Luik, A.J., et al., "Arterial Compliance in Patients on Long-Treatment-Time Dialysis," Nephrol. Dial Transplant, 1997; 12: pp. 2629-2632.

Mai, J.J., et al., "Strain Imaging of Internal Deformation," Ultrasound in Med. & Biol., 2002; vol. 28, Nos. 11/12: pp. 1475-1484.

Persson, M., et al., "Estimation of Arterial Pulse Wave Velocity With A New Improved Tissue Doppler Method," Proceeding of the 23rd Annual EMBS International Conference, 2001: pp. 188-191.

Taniwaki, H., et al., "Femoral Artery Wall Thickness and Stiffness in Evaluation of Peripheral Vascular Disease in Type 2 Diabetes Mellitus," Atherosclerosis, 2001; 158: pp. 207-214.

Timoshenko, S., et al., "Theory of Elasticity," 3rd Ed., McGraw Hill, New York, 1970.

* cited by examiner

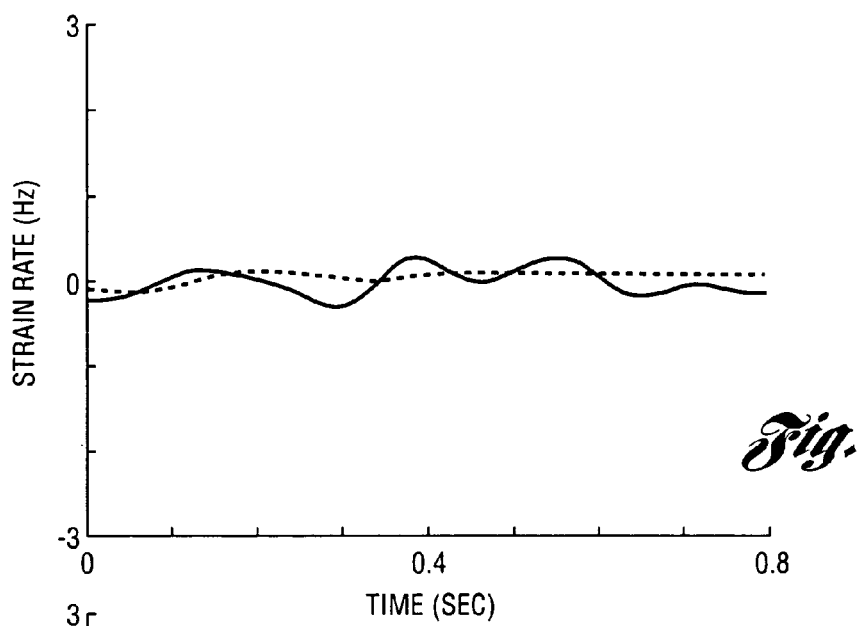
*Fig. 7a*
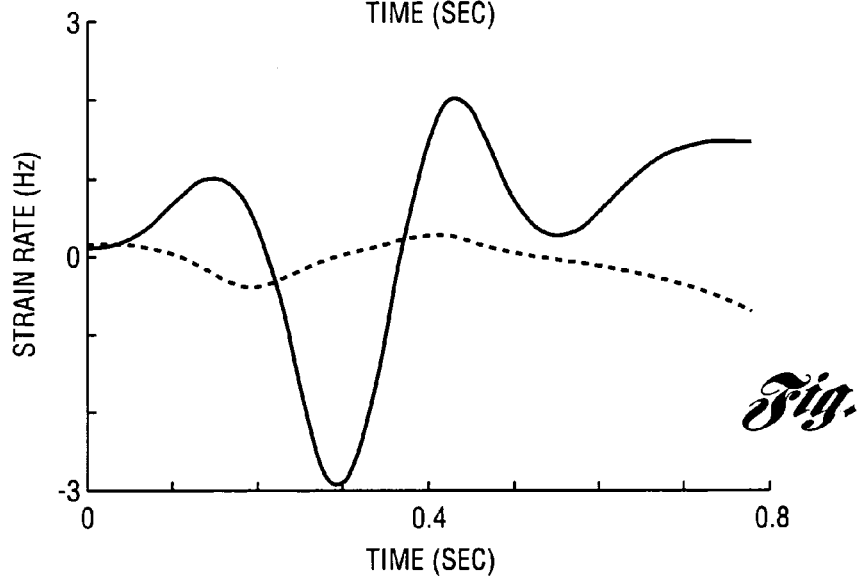
*Fig. 7b*
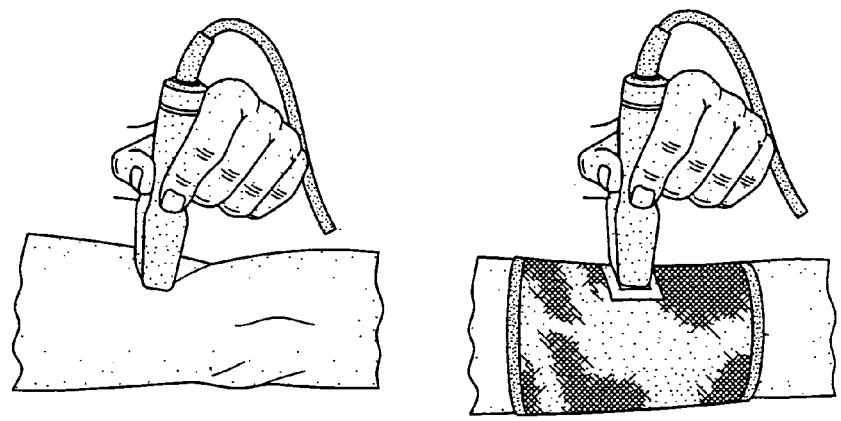
*Fig. 8a*  *Fig. 8b*

METHODS AND SYSTEMS FOR MEASURING MECHANICAL PROPERTY OF A VASCULAR WALL AND METHOD AND SYSTEM FOR DETERMINING HEALTH OF A VASCULAR STRUCTURE

STATEMENT REGARDING FEDERALLY SPONSORED RESEARCH OR DEVELOPMENT

This invention was made with Government support under NIH Grant Nos. DK-47324, HL-47401, HL-67647 and HL-68658. The Government has certain rights in the invention.

BACKGROUND OF THE INVENTION

1. Field of the Invention

This invention relates to methods and systems for measuring mechanical property of a vascular wall and a method and system for determining health of a vascular structure.

2. Background Art

The following references are referenced herein:

A. J. Bank et al., "In Vivo Human Brachial Artery Elastic Mechanics Effects of Smooth Muscle Relaxation," 1999; CIRCULATION 100:41-47;

D. H. Bergel, "The Static Elastic Properties of the Arterial Wall," J. PHYSIOL., 1961; 156:445-457;

C. Bilato et al., "Atherosclerosis and Vascular Biology of Aging," AGING (Milano) 1996; 8:221-234;

O. Bonnefous et al., "Non Invasive Echographic Techniques for Arterial Wall Characterization," IEEE ULTRASONIC SYMPOSIUM, 1996:1059-1064;

J. Blacher et al., "Carotidarterial Stiffness as a Predictor of Cardiovascular and All-Cause Mortality in End-Stage Renal Disease," HYPERTENSION, 1998; 32:570-574;

J. Blacher et al., "Impact of Aortic Stiffness on Survival in End-Stage Renal Disease," CIRCULATION 1999; 99:2434-2439;

O. Bonnefous et al., "New TDI Developments for Vascular and Cardiac Applications," IEEE ULTRASONIC SYMPOSIUM, 2000: 1285-1290;

A. Bruel et al., "Changes in Biomechanical Properties, Composition of Collagen and Elastin, and Advanced Glycation Endproducts of the Rat Aorta in Relation to Age," ATHEROSCLEROSIS 1996; 127:155-165;

D. Buprez et al., "Relationship Between Periventricular or Deep White Matter Lesions and Arterial Elasticity Indices in Very Old People," AGE AND AGEING, 2001; 30:325-330;

A. Eriksson et al., "Arterial Pulse Wave Velocity with Tissue Doppler Imaging," ULTRASOUND IN MED. & BIOL., 2002; Vol. 28, No. 5:571-580;

G. Faury, "Function-Structure Relationship of Elastic Arteries in Evolution: From Microfibrils to Elastin and Elastic Fibres," PATHOL. BIOL., 2001; 49:310-325;

Y. C. Fung, "Biomechanics: Mechanical Properties of Living Tissues," 2nd Ed., Spring-Verlag, 1993: 321-391;

G. Guerin et al., "Arterial Stiffening and Vascular Calcifications in End-Stage Renal Disease," NEPHRO DIAL TRANSPLANTATION, 2000; 15:1014-1021;

Hardung V., "Propagation of Pulse Waves in Visco-Elastic Tubing," AMERICAN PHYSIOLOGICAL SOCIETY, HANDBOOK OF PHYSIOLOGY, Section 2, Circulation, 1962, Vol. 1, eds., Hamilton, W. F. and Dow, P., 107;

D. R. Kaiser et al., "Brachial Artery Elastic Mechanics in Patients with Heart Failure," 2001; HYPERTENSION 38:1440-1445;

K. Konner et al., "The Arteriovenous Fistula," J. AM. SOC. NEPHROL., 2003; 14(6): 1669-80;

G. J. Langewouters et al., "The Static Elastic Properties of 45 Human Thoracic and 20 Abdominal Aortas In Vitro and the Parameters of a New Model," J. BIOMECH., 1984; 17-425-435;

M. A. Lubinski et al., "Speckle Tracking Methods for Ultrasonic Elasticity Imaging Using Short Time Correlation," IEEE TRANS. ULTRASON., FERROELECT., FREQ. CONTR., 1999, Vol. 46, pp. 82-96;

A. J. Luik et al., "Arterial Compliance in Patients on Long-Treatment-Time Dialysis," NEPHROL. DIAL TRANSPLANT, 1997; 12:2629-2632;

J. J. Mai et al., "Strain Imaging of Internal Deformation," ULTRASOUND IN MED. & BIOL., 2002; Vol. 28, Nos. 11/12:1475-1484;

M. Persson et al., "Estimation of Arterial Pulse Wave Velocity With A New Improved Tissue Doppler Method," PROCEEDING OF THE 23RD ANNUAL EMBS INTERNATIONAL CONFERENCE, 2001:188-191;

H. Taniwaki et al., "Femoral Artery Wall Thickness and Stiffness in Evaluation of Peripheral Vascular Disease in Type 2 Diabetes Mellitus," ATHEROSCLEROSIS, 2001; 158:207-214; and S. Timoshenko et al., "Theory of Elasticity," 3rd Ed., McGRAW HILL, New York, 1970.

Arterial compliance has been shown to be a strong indicator of vascular disease; cardiovascular disease, peripheral vascular occlusive disease, diabetes, and renal failure. Changes in the ratio of collagen to elastin in the extracellular matrix of the arterial media is believed to be one of the causes of arterial stiffness (Faury 2001; Bilato and Crow 1996; Bruel and Oxlund 1996). By measuring mechanical properties of tissue, elasticity imaging could non-invasively monitor vascular pathologies developing within the vascular wall. Previous attempts at non-invasive vascular elastic imaging include arterial wall motion estimation (Bonnefous et al., 1996; Taniwaki et al., 2001; Luik et al., 1997; Guerin et al., 2000), intraparietal strain imaging (Bonnefous et al., 2000) and pulse wave velocity measurement (Eriksson et al., 2002; Persson et al., 2001). Arterial compliance measurement was also conducted by monitoring internal pulsatile deformation in tissues surrounding the normal brachial artery (Mai and Insanna 2002). With some limits, these measurements have been correlated with clinical events including stroke (Buprez et al., 2001) and claudication symptoms (Taniwaki et al., 2001) in non-ESRD (End Stage Renal Disease) patients and adverse cardiovascular events in patients with ESRD (Blacher et al., 1998; Blacher et al., 1999), as well as length of time on dialysis (Luik et al., 1997).

One factor limiting the success of previously used methods is that arteries normally distended under physiologic pressure produce only small strain. The normal arterial wall, however, is a highly non-linear elastic medium, as illustrated by the solid curve in FIG. 1. The change of arterial elasticity due to intraluminal pressure was previously reported and analyzed over 40 years ago (Bergel 1961). FIG. 1 qualitatively captures the essential feature of nonlinear arterial wall compliance. Under physiologic loading, the mean arterial pressure produces a high effective elastic modulus in the wall. Consequently, the arterial pressure pulse only creates small radial strain (FIG. 1).

Another factor limiting the success of previous methods is that properties of the vessel as a whole or in cross-section are measured. In the previous reports on the arterial compliance over a wide range of intraluminal pressure (Bank et al., 1999; Kaiser et al., 2001), the compliance was inferred from the geometrical changes such as artery diameter and lumen cross-section based on a numerical model (Langewouters' model; Langewouters et al., 1984).

A phase-sensitive, two-dimensional speckle-tracking algorithm has been used by one of the co-inventors herein to determine displacements and strains (Lubinski et al., 1997).

SUMMARY OF THE INVENTION

An object of the present invention is to provide improved methods and systems for measuring mechanical property of a vascular wall and a method and system for determining health of a vascular structure wherein local deformation of a vessel wall resulting from physiologic pressures with altered transmural forces is measured.

Using local measures of strain, highly localized measurements can be made. These local measurements can be used individually or compiled into a "map" or "image" of the mechanical properties of the vessel wall. Consequently, the methods and systems have the capability of being "high resolution."

In carrying out the above object and other objects of the present invention, a method for measuring a mechanical property of a vascular wall which deforms in response to a transmural force under usual physiologic pressures is provided. The method includes altering the transmural force to obtain an altered transmural force. The method also includes measuring local deformation of the vascular wall resulting from physiologic pressures with the altered transmural force, and determining a value for the mechanical property based on a measured amount of local deformation.

The mechanical property may be a non-linear elastic property of the vascular wall.

The step of measuring may include the step of non-invasively, ultrasonically imaging the vascular wall.

The step of altering may include the step of reducing the transmural force to obtain a reduced transmural force.

The step of reducing may include the step of applying an external pressure to the vascular wall.

The external pressure may be substantially equal to a baseline internal pressure, and the vascular wall may deform by pulse pressure during a cardiac cycle.

The step of reducing may include reducing an internal pressure to the vascular wall.

The vascular wall may deform a relatively small amount in response to a transmural force under usual physiologic pressures and a relatively large amount in response to physiologic pressures with the altered transmural force.

The step of determining may include the step of directly estimating strain of the vascular wall.

Further in carrying out the above object and other objects of the present invention, a method for measuring a mechanical property of a vascular wall is provided. The vascular wall is characterized by a relationship of arterial pressure versus strain that exhibits a relatively large slope under physiologic pressure caused by an arterial pressure pulse having a first mean arterial pressure and that exhibits a relatively small slope under physiologic pressure caused by an arterial pressure pulse having a second mean arterial pressure. The method includes altering the first mean arterial pressure to obtain the second mean arterial pressure. The method further includes measuring local deformation of the vascular wall at the second mean arterial pressure, and determining a value for the mechanical property based on the measured amount of local deformation.

The step of measuring may include the step of non-invasively, ultrasonically imaging the vascular wall.

The step of altering may include the step of reducing the first mean arterial pressure to obtain the second mean arterial pressure.

The step of reducing may include the step of applying an external pressure to the vascular wall.

The external pressure may be substantially equal to a baseline internal pressure, and the vascular wall may deform by pulse pressure during a cardiac cycle.

The step of reducing may include reducing an internal pressure to the vascular wall.

The step of determining may include the step of directly estimating strain of the vascular wall.

Still further in carrying out the above object and other objects of the present invention, a method is provided for determining health of a vascular structure which includes a vascular wall which deforms in response to a transmural force under usual physiologic pressures. The method includes altering the transmural force to obtain an altered transmural force. The method further includes measuring local deformation of the vascular wall resulting from physiologic pressures with the altered transmural force, and determining the health of the vascular structure based on the measured amount of local deformation.

The step of measuring may include the step of ultrasonically imaging the vascular wall.

The step of altering may include the step of reducing the transmural force to obtain a reduced transmural force.

The step of reducing may include the step of applying an external pressure to the vascular wall.

The external pressure may be substantially equal to a baseline internal pressure, and the vascular wall may deform by pulse pressure during a cardiac cycle.

The step of reducing may include reducing an internal pressure to the vascular wall.

The vascular wall may deform a relatively small amount in response to a transmural force under usual physiologic pressures and a relatively large amount in response to physiologic pressures with the altered transmural force.

The step of determining may include the step of directly estimating strain of the vascular wall.

Yet still further in carrying out the above object and other objects of the present invention, a system for measuring a mechanical property of a vascular wall which deforms in response to a transmural force under usual physiologic pressures is provided. The system includes means for altering the transmural force to obtain an altered transmural force. The system further includes means for measuring local deformation of the vascular wall resulting from physiologic pressures with the altered transmural force, and means for determining a value for the mechanical property based on the measured amount of local deformation.

The mechanical property may be a non-linear elastic property of the vascular wall.

The means for measuring may include means for non-invasively, ultrasonically imaging the vascular wall.

The means for altering may include means for reducing the transmural force to obtain a reduced transmural force.

The means for reducing may include means for applying an external pressure to the vascular wall.

The external pressure may be substantially equal to a baseline internal pressure, and the vascular wall may deform by pulse pressure during a cardiac cycle.

The means for reducing may include means for reducing an internal pressure to the vascular wall.

The vascular wall may deform a relatively small amount in response to a transmural force under usual physiologic pressures and a relatively large amount in response to physiologic pressures with the altered transmural force.

The means for determining may include means for directly estimating strain of the vascular wall.

Still further in carrying out the above object and other objects of the present invention, a system is provided for measuring a mechanical property of a vascular wall. The vascular wall is characterized by a relationship of arterial pressure versus strain that exhibits a relatively large slope under physiologic pressure caused by an arterial pressure pulse having a first mean arterial pressure and that exhibits a relatively small slope under physiologic pressure caused by an arterial pressure pulse having a second mean arterial pressure. The system includes means for altering the first mean arterial pressure to obtain the second mean arterial pressure. The system further includes means for measuring local deformation of the vascular wall at the second mean arterial pressure, and means for determining a value for the mechanical property based on the measured amount of local deformation.

The means for measuring may include means for non-invasively, ultrasonically imaging the vascular wall.

The means for altering may include means for reducing the first mean arterial pressure to obtain the second mean arterial pressure.

The means for reducing may include means for applying an external pressure to the vascular wall.

The external pressure may be substantially equal to a baseline internal pressure, and the vascular wall may deform by pulse pressure during a cardiac cycle.

The means for reducing may include the means for reducing an internal pressure to the vascular wall.

The means for determining may include means for directly estimating strain of the vascular wall.

Still further in carrying out the above object and other objects of the present invention, a system for determining health of a vascular structure including a vascular wall which deforms in response to a transmural force under usual physiologic pressures is provided. The system includes means for altering the transmural force to obtain an altered transmural force. The system further includes means for measuring local deformation of the vascular wall resulting from physiologic pressures with the altered transmural force, and means for determining the health of the vascular structure based on the measured amount of local deformation.

The means for measuring may include means for non-invasively, ultrasonically imaging the vascular wall.

The means of altering may include means for reducing the transmural force to obtain a reduced transmural force.

The means for reducing may include means for applying an external pressure to the vascular wall.

The external pressure may be substantially equal to a baseline internal pressure, and the vascular wall may deform by pulse pressure during a cardiac cycle.

The means for reducing may include means for reducing an internal pressure to the vascular wall.

The vascular wall may deform a relatively small amount in response to a transmural force under usual physiologic pressures and a relatively large amount in response to physiologic pressures with the altered transmural force.

The means for determining may include means for directly estimating strain of the vascular wall.

The local deformation for the above methods and systems may be an intramural deformation.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 7a and 7b are graphs showing strain rate over one cardiac cycle; under physiologic pressure (i.e., FIG. 7a), healthy (solid) and diseased (dashed) arteries are hard to distinguish; after pressure equalization (i.e., FIG. 7b), diseased (dashed) artery can be easily differentiated from healthy (solid) one;

FIGS. 8a and 8b are schematic diagrams showing scanning of an upper arm without (i.e., FIG. 8a) and with (i.e., FIG. 8b) a blood pressure cuff; while imaging the cross-section of the brachial artery and collecting ultrasound data frame-by-frame, surface compression was performed; the applied external pressure over the range of physiologic pressure is comparable to the pressure that would be generated in measuring a subject's blood pressure; both FIGS. 8a and 8b illustrate enough pressure equalization effect to bring the artery into the low preload region; external force can be monitored by a manometer attached to the cuff in FIG. 8b;

in semi-log scale and strain represents $\bar{\varepsilon}$; open circles are represented moduli and solid line is the fit for the normal subject; open squares are reconstructed moduli and dashed line is the fit for the subject with known vascular disease.

DETAILED DESCRIPTION OF THE PREFERRED EMBODIMENTS

Figure 1:
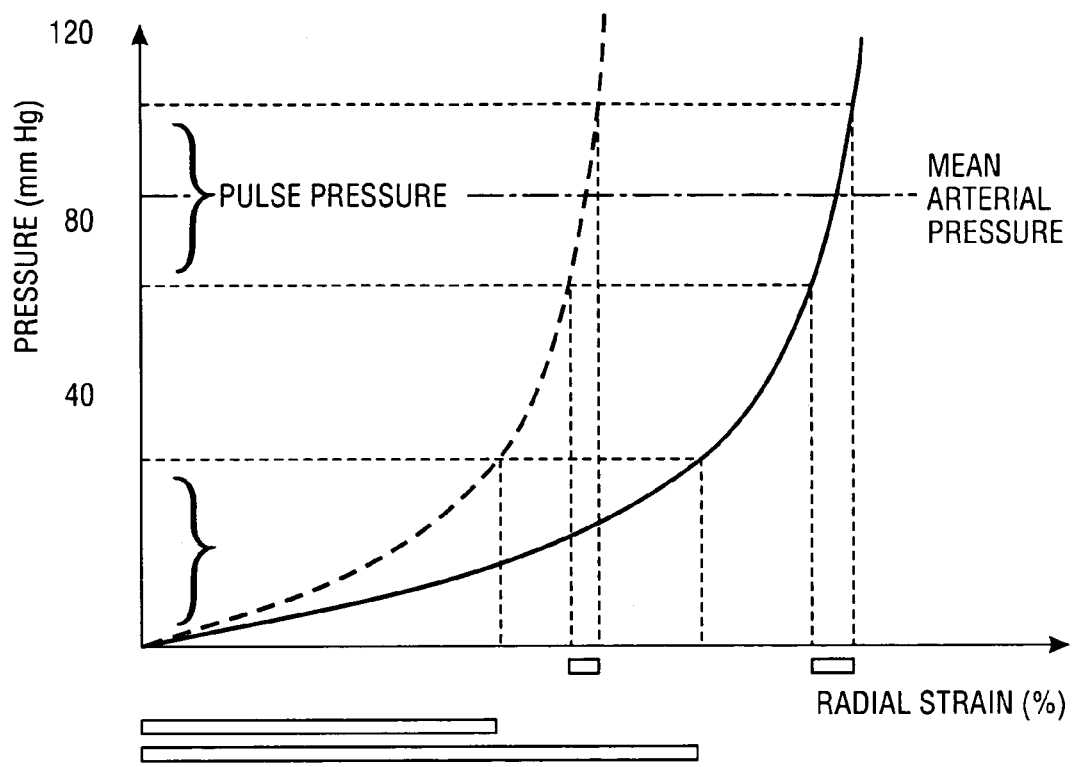
FIG. 1 is a graph illustrating arterial elasticity characteristics at different preload; the solid curve represents normal tissue, and the dashed curve represents less compliant diseased tissue.

As previously mentioned, one of the significant obstacles of measuring mechanical properties of blood vessels is that vascular wall deformations under physiologic pressures only exhibit small deformations with the usual (physiologic) forces applied. By altering the forces across a vessel wall (transmural=across the vessel wall), the deformations induced from physiologic pressure across the arterial wall is altered with the methods and systems of the present invention. By measuring the local deformations, which may be intramural deformations, with altered transmural forces, new and detailed measurements can be made about the mechanical properties of the vessel.

In other words, one of the significant obstacles of measuring mechanical properties of blood vessels (arteries, veins, fistulae or other blood transporting structures hereafter referred to as "vessel" [noun] or "vascular" [adjective]) in the body (in-vivo) is that vascular wall deformations under physiologic pressures only exhibit small deformations with the usual (physiologic) forces (or pressures) applied. By altering the transmural forces across a vessel wall (transmural=across the vessel wall), the changes induced (deformation=changes in position of at least one location within the vessel wall) from physiologic pressure across the arterial wall is altered. By measuring the deformations with altered transmural forces, new and very detailed measurements can be made about the mechanical properties of the vessel. These measurements are derived from deformations induced by the altered forces. In particular, non-linear elastic properties of the vessel wall can be measured with great accuracy and precision if large wall deformations (e.g., 20%) are induced. Non-linear elastic properties are directly related to many pathologies altering vascular compliance and, so, there should be numerous applications of a truly non-invasive method to monitor this physiologically significant parameter.

The measurements include an parameter that can be derived from (1) altering the transmural forces (or pressures), and (2) measuring the local deformation that results from physiologic forces. These measurements include, but are not limited to: displacement, strain, elastic moduli (e.g., Young's modulus), time derivatives (e.g., strain rate) or other mathematical operations or manipulations used to derive values from the measured local deformation. Consequently, an important aspect of the invention is measuring the local deformation of the vessel wall resulting from physiologic pressures with altered transmural force.

The means of altering the transmural forces may be highly variable and include: external pressure applied to the vessel directly or applied to tissues overlying or surrounding the vessel such as, but not limited to: (1) manual compression (e.g., external compression with the hand, or the hand holding an object), (2) other-methods of external compression such as a cuff inflated to apply pressure (such as, but not limited to a blood pressure cuff around an arm or leg), (3) internally "pressing" with a balloon or other internal structure that change geometry in such a way as to alter the transmural forces of a vessel, (4) maneuvers that alter forces such as straining against a closed airway (Valsalva maneuver) or blowing or sucking air against resistance, all of which change intra-thoracic pressure, alter blood flow in blood vessels with the thoracic cavity as well as blood entering and leaving the thoracic cavity, and thereby may change the transmural pressure (forces) of the vessel and allow the necessary measurements to be made, and (5) pharmacologic agents may be administered that alter blood pressure and thereby may be used to alter the transmural pressure, or (6) any other means of altering transmural vascular forces.

The preferred means of measuring the local deformation uses data generated from ultrasound imaging. However, other means of measuring the deformation will allow calculation of the mechanical properties of the vessel. These other means of measuring the deformation may include, but are not limited to: (1) visual inspection, (2) manual measurement either directly or indirectly from images generated of the deformations from any imaging system, (3) sensing any location within the vessel wall with any method or device (such as, but not limited to, any wavelength electromagnetic radiation including, but not limited to, X-ray, CT, or measuring other physical parameters that allow the movement or position of the vessel wall to be measured such as MRI, or any imaging modality). All that is important is to measure the location of the vessel wall to determine the local deformation from baseline (physiologic) pressures (forces) while the altered forces are generated.

As described herein, the mean arterial pressure is lowered to reduce the preload so that the arterial pressure pulse creates much larger strain (FIG. 1). The inherent elastic nonlinearity of the arterial wall provides an opportunity to greatly expand the strain dynamic range by manipulating the mean arterial pressure.

By lowering mean arterial pressure, it is much easier to differentiate diseased from normal arterial wall. Almost all arterial pathologies decrease compliance, as illustrated qualitatively by the dashed curve in FIG. 1. At low arterial mean pressure (FIG. 1), the difference in radial strain between normal and diseased arteries is much larger than at high mean pressure (FIG. 1). An elasticity imaging procedure exploiting this relationship for highly sensitive characterization of arterial compliance is described herein.

Arterial elasticity can be more accurately determined by measuring localized intramural strain. As described herein, the intramural radial normal strain is directly estimated using a phase-sensitive, two-dimensional speckle-tracking algorithm to determine displacements and strains (Lubinski et al., 1997). In a clinical setting, larger arterial strains with corresponding higher strain signal-to-noise ratio (SNR) are demonstrated using free-hand deformation to induce transmural pressure equalization and reduce preload. Strain and strain rate measurements at maximum pulsation correspond to the compliance of the artery under the same condition that blood pressure is taken with a blood pressure cuff. The feasibility of this technique is demonstrated using ex- and in-vivo measurements, and a straightforward elasticity reconstruction algorithm is presented to quantitatively assess the results.

An example of preferred method of performing the measurement and resulting tenfold change in mechanical property (strain) measured is now described.

Peripheral Arterial Strain Imaging Using External Pressure Equalization

Non-invasive peripheral arterial ultrasound strain imaging was performed while applying external pressure to induce changes in the baseline pressure difference across the arterial wall. By equalizing the baseline internal and external arterial pressure during the ultrasound measurement, increased arterial strains are induced by the relatively stable pulse pressure (pulse pressure=systolic pressure—diastolic pressure) during the cardiac cycle. The brachial and radial arteries of a 43 year old man were imaged with a 7.2 MHz linear ultrasound transducer while external deformations were continually increased over several cardiac cycles. External pressure was increased until the arteries collapsed during diastole, but distended during systole when the applied force exceeded the internal reference pressure of 80 mmHg (subject's diastolic pressure). Correlation-based, phase-sensitive, two-dimensional speckle-tracking algorithm was employed to calculate strain and strain rate from the internal displacement of the artery wall.

Imaging of the arteries without external deformation resulted in measured strains up to 2% over the cardiac cycle. When applied pressure matched the internal baseline diastolic pressure of 80 mmHg, the strains increased by a factor of 10 with peak strains of 20% over the cardiac cycle. In addition, the peak strain rate under physiological conditions ranged from 0.1 $sec^{-1}$ during diastole to -0.2 $sec^{-1}$ during systole. After arterial pressure equalization, the peak strain rate increased to 1.0 $sec^{-1}$ during diastole and -2.5 $sec^{-1}$ during systole, similar to the increase in peak strains. By applying external pressure, the pressure difference across the arterial wall at baseline (diastole) is reduced, while the pressure change from diastole to systole remains stable. As a result, the preload on the arterial wall can be decreased to near zero, leading to maximal strain during the cardiac cycle. By varying the external pressure, the range of measured strains vary over a cardiac cycle, and the non-linear properties of the arterial wall may be better characterized. Methods such as this that elicit the non-linear properties of the arterial wall could be used to better characterize vascular pathologies such as vessel hardening, neointimal hyperplasia, and vulnerable plaques.

As shown in FIG. 1, if the mean arterial pressure can be lowered, then the arterial pressure pulse can create much larger strain. The inherent elastic non-linearity of the arterial wall provides an opportunity to greatly expand the strain dynamic range if the mean arterial pressure can be manipulated.

By lowering mean arterial pressure, it is much easier to differentiate diseased from normal arterial wall. Almost all arterial pathologies decrease compliance, as illustrated by the dashed curve in FIG. 1. At low arterial mean pressure, the difference in radial strain between normal and diseased artery is much larger than at high mean pressure. The focus here is to develop an elasticity imaging procedure exploiting this relationship for highly sensitive characterization of arterial compliance.

Arterial elasticity can be more accurately determined by intramural strain. Preferably, the intramural radial normal strain is directly estimated.

As described hereinbelow, in a clinical setting, larger arterial strains with corresponding higher strain signal-to-noise ratio (SNR) is demonstrated using free-hand deformation to induce transmural pressure equalization. Strain and strain rate measurements at maximum pulsation correspond to the compliance of the artery under the same condition that blood pressure is taken with a blood pressure cuff. The feasibility of this technique is demonstrated using ex- and in-vivo measurements.

Methods

Like any other tissue, arteries exhibit non-linear elasticity (Fung 1993). To demonstrate and quantify arterial non-linearity with respect to internal loading, a controlled experimental protocol was designed. The intramural strain of an ex-vivo bovine artery was measured when the internal pressure was increased by a fluid-filled syringe pump.

Figure 2:
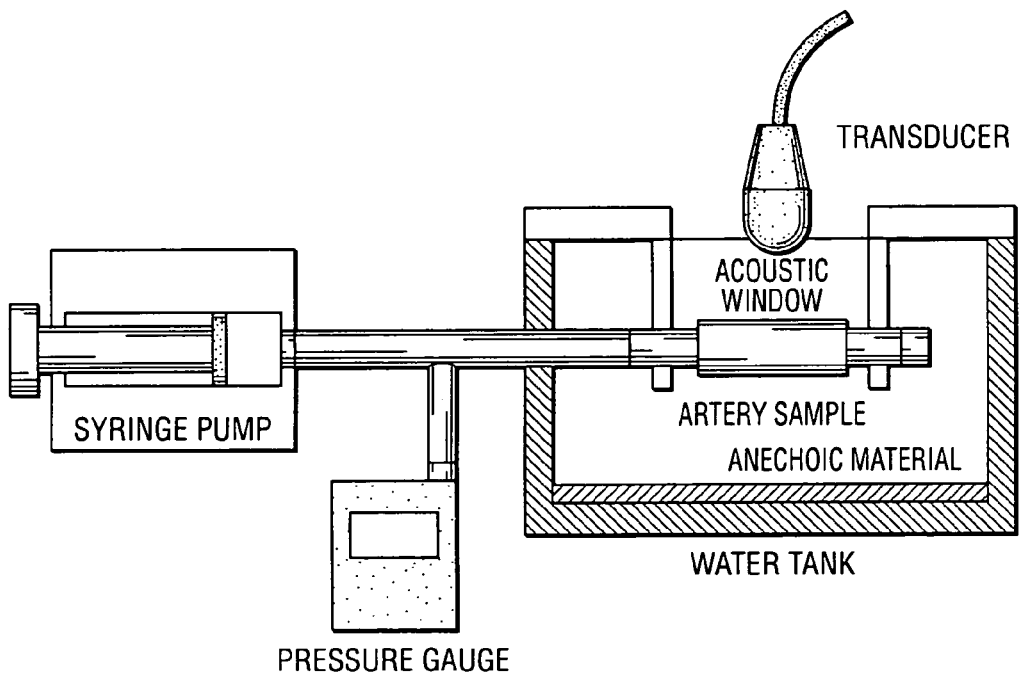
FIG. 2 is a schematic view of an experimental set-up for ex-vivo arterial elasticity measurements.

Experimental Set-Up. A closed-loop compression system was designed to pressurize an artery sample while simultaneously scanning with ultrasound. A programmable commercial syringe pump (Cole-Parmer) serves as a pressure source. An acoustic window is designed to hold an arterial sample between inlet and outlet ports. The outlet is sealed so that the internal pressure develops while the syringe pump compresses. A pressure gauge is placed between the syringe and artery sample close to the artery to measure intraluminal pressure. The acoustic window is placed in a water tank with anechoic material at the bottom to suppress possible reverberation, and the tank is placed underneath an ultrasound transducer positioning device. A PC-based RF data acquisition system is connected to a commercial ultrasound scanner (Siemens Elegra). A block diagram is presented in FIG. 2.

Bovine Artery ex-vivo. A 50 mm-long bovine carotid artery segment preserved in 30% ethanol (Artegraft, Brunswick, N.J.) was placed in the middle of the acoustic window connected to the flow path filled with degassed water. A commercial (Cole-Parmer) syringe pump was programmed to pump water at a fixed rate over a fixed period (70.5 ml/min. for 13 seconds) to build intraluminal pressure to 120 mmHg. While the artery distended from the resting position, a 12.0 MHz linear ultrasound array connected to a commercial ultrasound scanner (Siemens Elegra) imaged the arterial cross-section at a rate of 22 frames per second for 13 seconds. RF data from every frame in the sequence were captured. The intraluminal pressure over time was also recorded. Data were subsequently processed using a phase-sensitive, two-dimensional speckle-tracking algorithm to determine displacements and strains (Lubinski et al., 1997). Correlation-based algorithms were used to track internal displacements. Frame-to-frame lateral and axial displacements were estimated from the position of the maximum correlation coefficient, where the correlation kernel size equaled the speckle spot for optimal strain estimation and axial displacements were refined using the phase zero-crossing of the complex correlation function. Frame-to-frame displacement estimates were integrated from and registered to the initial coordinate system (i.e., Lagrangian presentation). Spatial derivatives of the displacements were computed in one region of the artery to estimate the radial normal strain (i.e., the radial derivative of the radial displacement). As described hereinbelow, the radial normal strain is called simply the strain, where appropriate.

Humian Artery in-vivo. Two subjects were tested. The first was a 43 year old healthy male volunteer and the second was a 48 year old male with ESRD secondary to diabetes mellitus, on hemodialysis, and a history of peripheral vascular occlusive disease, with prior right below the knee amputation.

A 7.2 MHz linear array was used with continuous freehand compression performed on the surface of the right upper arm close to the brachial artery. While imaging the cross-section of the brachial artery at a rate of 107 frames per second and collecting ultrasound data frame-by-frame, surface compression was performed by the investigators. The applied external force produces internal pressure comparable to that generated in measuring a subject's blood pressure. The compression was increased until brachial artery pressure exceeded diastolic pressure, as evidenced by viewing B-scan images. Collected RF data were processed off-line in the same way as described above.

Results

Figure 4:
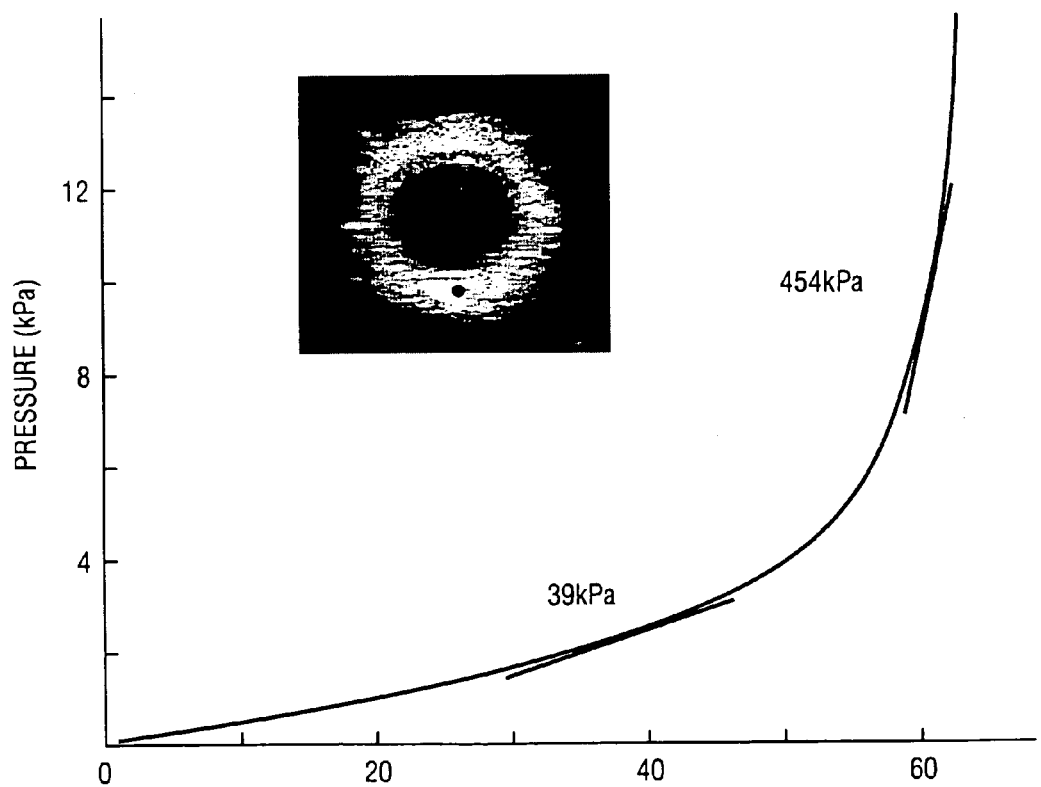
FIG. 4 is a graph of a pressure-strain curve for a bovine carotid artery; the lumen radius was 3.5 mm and the advential surface radius was 4.25 mm; the strain in the plot represents the radial normal strain in the middle layer of the artery wall as indicated by the dot in the inserted cross-sectional image.

Bovine Artery ex-vivo. The accumulated displacement and axial normal strain within the artery wall were referenced to a frame where the artery was at rest. Representative image frames over the full pressure range are presented in FIG. 3. From the resting position of the bovine artery at 0 mmHg internal pressure, the syringe pump pressurized the lumen to 120 mm-Hg. The pressure is plotted in FIG. 4 versus axial normal strain at the arterial bottom wall, approximating the radial strain. The strain initially increases rapidly with pressure and then hardly changes. Assuming incompressibility and plane strain in the cross-section of the artery, the radial normal strain, $\epsilon_r$, on the artery wall can be expressed as a function of internal pressure, $p_i$, outside pressure, $p_o$ and Young's modulus, E (Appendix A and FIG. 11):

$$\varepsilon \equiv \varepsilon_r = \frac{3a^2b^2}{2(b^2-a^2)r^2}\left(\frac{p_o - p_i}{E}\right), a < r < b, \quad (1)$$

where a is the lumen radius, b is outer radius of the artery, and r is the strain measurement point. Using this relation, E can be estimated as a function of $\epsilon$. In this experiment, outside pressure, $p_o$ can be ignored because the artery sits less than 2.5 cm from the surface of the water. As illustrated in FIG. 4, the elastic modulus at low preload (E=39 kPa at 40% preload, representing an intramural pressure of about 3 kPa) is over an order of magnitude smaller than that at physiologic preload (E=454 kPa at 60% preload, representing an intramural pressure of about 10 kPa). This implies that the artery in the physiologic region produces only 1/10 of the strain in the low-preload (i.e., after pressure equalization) region for the same pressure differential. Because it is difficult to distinguish diseased from normal arteries with small strain under physiologic pressure, it is important to bring the artery into the low-preload region to better determine its elasticity through strain measurement. By applying external force opposite to that generated by the mean arterial pressure, higher strains may enable easier differentiation of diseased arteries from normal ones.

Figure 5:
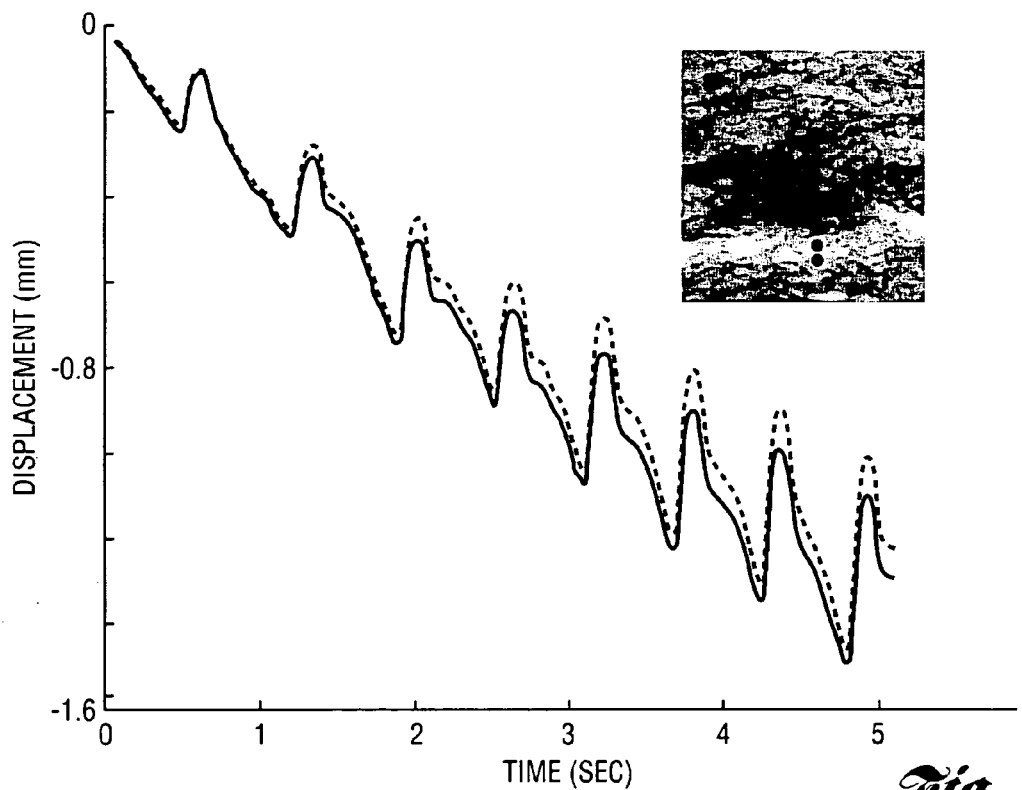
FIG. 5 are graphs which show accumulated radial displacement of two points on the artery wall of a healthy volunteer indicated by the two dots in the inserted cross-sectional image of a healthy volunteer; the dashed line represents the accumulated radial displacement of the point closer to the transducer and the solid line is for the point further away from the transducer; all lines are fit using cubic spline smoothing within an error of ±0.01 mm.

Human Artery in-vivo. The accumulated radial displacement of the brachial artery wall was estimated relative to the original frame, as illustrated in FIG. 5, where results are compared from two points in the wall of the normal subject separated by 0.2 mm. The overall slope of the average displacement signals compression by the transducer. Cyclic displacement represents deformation by the pulse pressure. The point on the bottom wall closer to the transducer displaced more than the point further away from the transducer at systole and both points come back to the resting position at diastole. This shows that the artery wall compresses maximally at systole and returns to the resting position at diastole.

Figure 6A:
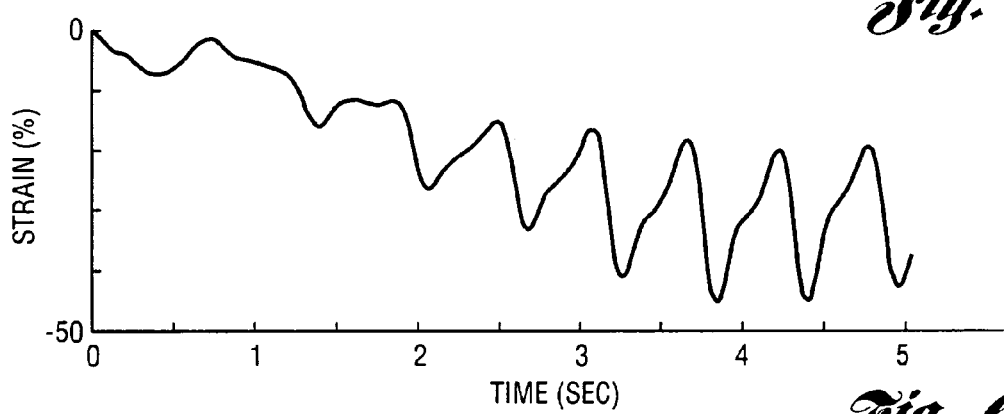
FIGS. 6a and 6b are graphs of radial strain and strain rate, respectively, of a healthy volunteer with continuous external compression.
Figure 6B:
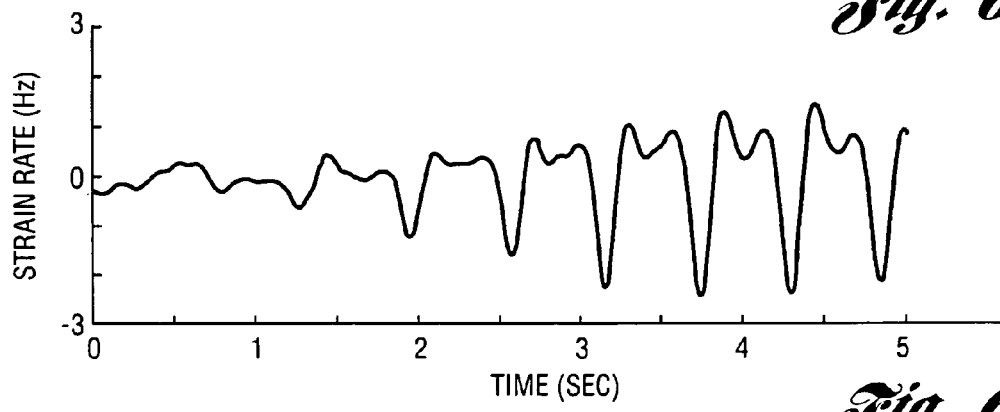

Based on the displacement information depicted in FIG. 5, radial normal strain and strain rate were estimated. When the applied pressure matched the internal baseline diastolic pressure of 80 mmHg, strains increased by a factor of 10 with peak strains of 20% over a cardiac cycle (FIG. 6a). In addition, the strain rate computed from the accumulated displacements increased over several cardiac cycles. The peak strain rate under physiologic conditions ranged from 0.1 Hz during diastole to −0.2 Hz during systole. After arterial pressure equalization, the peak strain rate increased to 1.0 Hz during diastole and −2.5 Hz during systole, similar to the increase in peak strains (FIG. 6b). By equalizing the baseline arterial pressure to approximate the diastolic pressure, the preload on the arterial wall decreases to zero, resulting in maximal strain. The elastic properties of the arterial wall can be better characterized with intramural strain measurements extending over a large preload range.

The radial normal strain and strain rate of the diseased subject are compared with those of the normal, over approximately one cardiac cycle in FIGS. 7a and 7b. FIG. 7a illustrates differences at high preload (i.e., physiologic condition), and FIG. 7b at an intraluminal pressure nearly equalized by the applied force (i.e., low preload). Overall, the artery of the diseased subject produces smaller strain and strain rate than the artery of the normal. Pulse pressure of each subject was recorded by measuring blood pressure before and after the ultrasound scan. The blood pressure of the diseased subject was 160/85 mmHg while the normal subject measured 114/78 mmHg. Noting that the pulse pressure (Δp=75 mmHg) of the diseased subject is twice as big as the normal subject (Δp=36 mmHg), the strain and strain rate contrast will be doubled after normalization by the pulse pressure. These results demonstrate that differences in elastic properties between the two subjects become more pronounced when measured in the low-preload region by this pressure equalization procedure.

Figure 3:
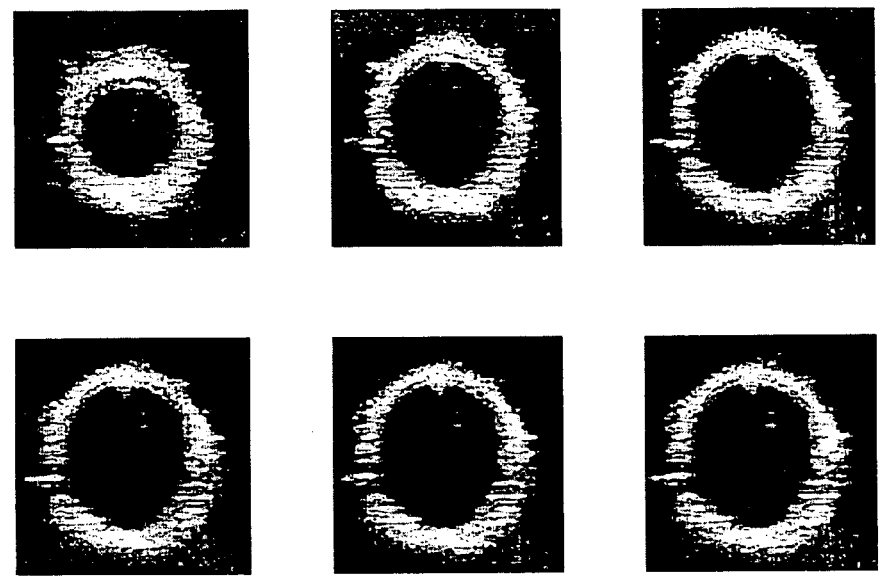
FIG. 3 illustrates representative image frames of a bovine carotid artery at different intraluminal pressures; from the top-left, pressure increases clockwise; the top three are in the low-preload region and the bottom three are in the high-preload region; each picture is separated by the same time interval; determining E from the arterial artery is very hard in the high-preload region because the arterial diameter hardly changes for a given pressure differential.

Elastic Modulus Reconstruction. For an isolated artery, Equation (1) can be used to reconstruct the arterial elastic modulus over the entire strain range, as illustrated in FIG. 3. However, in-vivo measurements cannot use this simple formulation since the artery is attached to surrounding tissue. If surrounding tissue can be modeled as a continuous medium with elastic modulus $E_2$, and the artery wall is considered homogeneous with an elastic modulus $E_1$, then the radial strain can be written as (Appendix B and FIG. 12):

$$\varepsilon \equiv \varepsilon_r = \left[\frac{-3a^2b^2 p_i}{2(b^2-a^2)r^2}\right] / \left[E_1 + \frac{a^2}{(b^2-a^2)}E_2\right] \quad (2)$$

To reconstruct the modulus, this equation must be inverted, $$\left[E_1 + \frac{a^2}{(b^2-a^2)}E_2\right] = \left[\frac{-3a^2b^2 p_i}{2(b^2-a^2)r^2}\right]\left[\frac{p_i}{\varepsilon}\right] \quad (3)$$

As a first step in solving this equation, a, b, and r must be estimated from B-scan images. In this study, the constants were computed by hand, but in real-time clinical operation it is very feasible to design automatic lumen detecting algorithms to define both intimal and advential boundaries (i.e., a and b). To determine a, b, and r, the averaging procedure was used in this study because artery was not perfectly circular over the entire pressure equalization procedure. This averaging should not introduce significant error into the estimated modulus as long as a and b change at the same rate for the reasonably small deformation.

Figure 9:
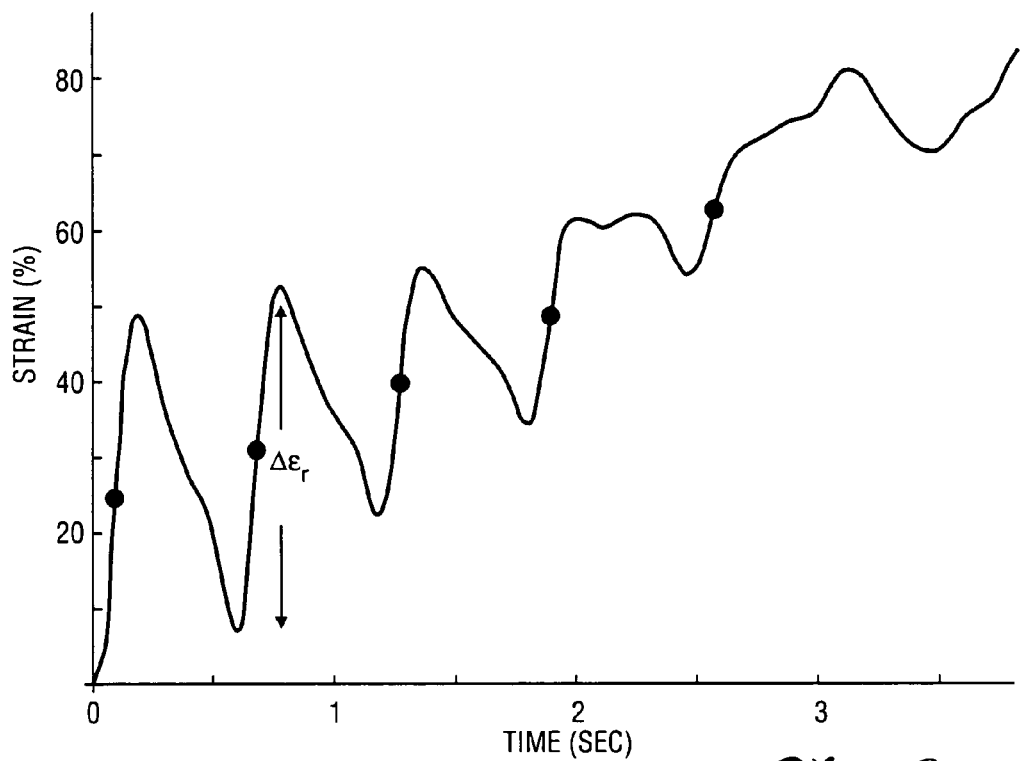
FIG. 9 is a graph-which illustrates radial normal strain referenced to the arterial geometry at maximum pulsation; the closed circles represent mean strain at each cardiac cycle, $\bar{\epsilon}$.

Given a and b and the coordinates of the strain measurement position, the radius r can also be captured automatically. Consequently, Equation (3) can be written as:

$$E_1 + K_2 E_2 = K_1 \left[ \frac{\Delta p}{\Delta \varepsilon} \right], \quad (4)$$

where $$K_1 = \frac{-3a^2 b^2}{2(b^2 - a^2) r^2}, K_2 = \frac{a^2}{(b^2 - a^2)}$$

are geometric factors computed from B-scan images. $\Delta p$ is pulse pressure and $\Delta \varepsilon$ is inter-cardiac strain (i.e., change in strain from systole to diastole). The strain (FIG. 6a) for the normal subject referenced to the arterial geometry at high preload (under physiologic pressure) is converted into the strain referenced to the arterial geometry at low preload (after pressure equalization) to conform to the normal geometry used to compute non-linear elastic parameters. That is, the reference frame must be converted to the one closest to the undistended arterial geometry to present Lagrangian strain for nonlinear analysis similar to that presented in FIG. 4 for the isolated artery. This means frame-to-frame displacements must be accumulated "backwards" from the last frame to the first, yielding the final simple expression relating the strain relative to the first frame ($\Delta_i^o$ for the $i^{th}$ frame) to the strain relative to the last frame ($E_i$ for the $i^{th}$ frame):

$$\varepsilon_i = \frac{\varepsilon_{N-i+1}^o - \varepsilon_N^o}{1 + \varepsilon_N^o}, \quad (5)$$

where $\Delta_N^o$ is the maximum original strain at the pressure equalization frame (FIG. 9).

Figure 10:
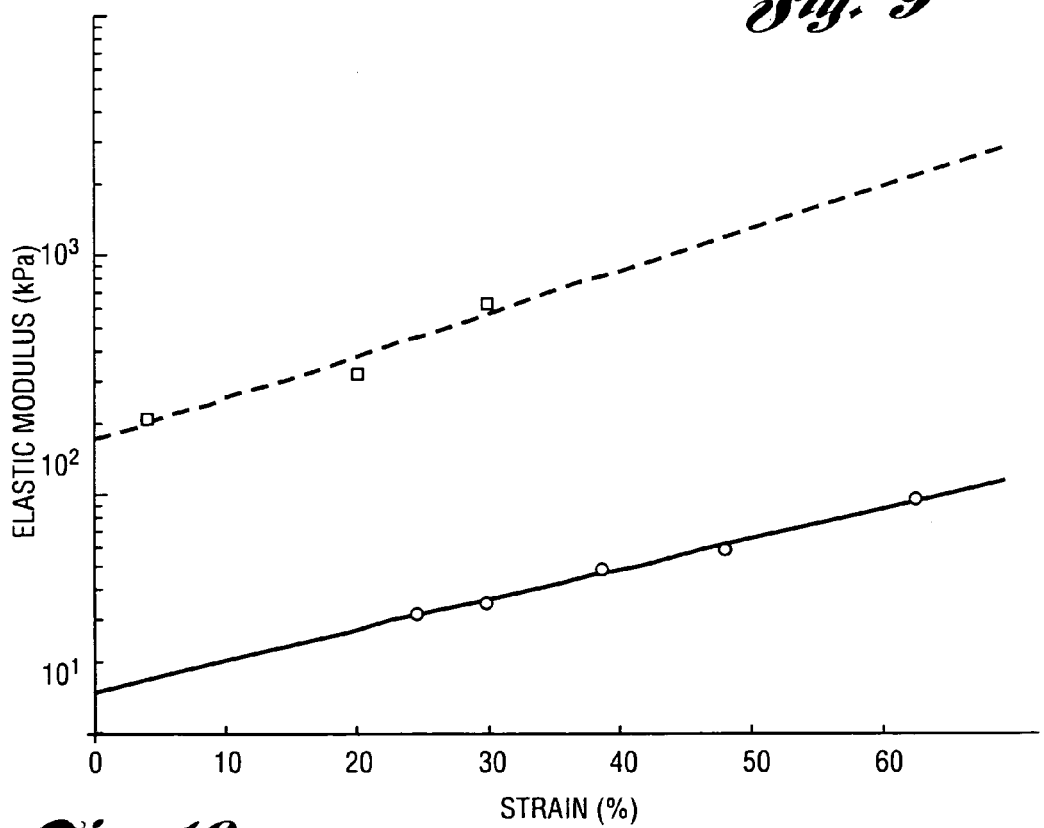
FIG. 10 shows graphs which illustrate arterial elastic modulus reconstruction; elastic modulus represents $$K_1\left[\frac{\Delta p}{\Delta \varepsilon}\right]$$

Inter-cardiac strain of varying amplitude developed over each cardiac cycle $\Delta \varepsilon$ and corresponding mean strain $\bar{\varepsilon}$ was calculated from FIG. 9. With intimal and advential boundaries, a and b, and the coordinates of the strain measurement position, r estimated from B-scan images, $$K_1 \left[ \frac{\Delta p}{\Delta \varepsilon} \right]$$

from Equation (4) is plotted on a semi-log scale versus mean strain at each cardiac cycle, $\bar{\varepsilon}$ (FIG. 10). The pulse pressure measured before and after the experiment, $\Delta p$, was assumed to be constant over cardiac cycles. The reconstructed elastic moduli were fit to a straight line. If the elastic modulus of the surrounding muscle, $E_2$, can be considered small compared to the arterial elastic modulus, the intercept will determine the undistended (i.e., zero preload) in-vivo arterial elastic modulus. Otherwise, the elastic modulus of surrounding muscle must be measured to correctly reconstruct the arterial elastic modulus, which is overestimated by $K_2 E_2$. However, if change in elastic modulus with preload is small for surrounding tissue compared to that of the artery wall, then the slope of this curve (i.e. nonlinear coefficient for a purely exponential model) will be correctly reconstructed independent of the elastic modulus of the surrounding medium. For the normal subject, the intercept ranges from 14.7 kPa to 16.5 kPa, and the slope is 2.9 within an error of ±0.1. The intercept ranges from 153.2 kPa to 193.7 kPa, and the slope is 4.0 within an error of ±0.6 for the subject with known vascular disease. The undistended elastic modulus of the diseased subject is over ten times that of the normal subject. The ratio of the elastic modulus of the diseased artery over the normal artery will only increase when accounting for the overestimation by $K_2 E_2$ from the surrounding tissue, which is assumed to be small compared to $E_1$. Since the surrounding tissue modulus may be comparable between subjects, the overestimation for the diseased subject is much less pronounced than that for the normal subject. In addition, the nonlinear coefficient (slope in FIG. 10) is more increased for the diseased subject.

The nonlinear coefficient can serve as a strong indicator of arterial stiffness. To estimate this parameter with optimal accuracy, all image frames from high preload to low must be used. One limitation of the present study was that all image frames for the diseased subject were not of high enough quality to contribute to this accumulation. Consequently, high precision intramural strain was computed over several non-consecutive cardiac cycles in the image sequence. An absolute geometric reference was established between isolated segments by tracking changes in arterial wall thickness over the entire sequence using B-scan images. These lower precision measurements only provided the geometrical reference for high precision intramural strain measurements. Nevertheless, the results presented in FIG. 10 show that good results can be obtained from intramural measurement even when all image frames are not of sufficient quality for high precision phase-sensitive speckle tracking.

Discussion and Summary

The intramural strain range in peripheral arteries produced by the pulse pressure can be significantly extended by simply applying pressure comparable to a subject's blood pressure. Intramural strain can be monitored directly with high precision using phase-sensitive ultrasonic speckle tracking algorithms developed for elasticity imaging. By combining pressure equalization with phase-sensitive speckle tracking, new diagnostic information may be gathered about the non-linear elastic properties of the arterial wall. As demonstrated experimentally herein, the radial strain and strain rate increased ten-fold in a healthy artery when mean arterial pressure is reduced from physiologic levels. The deformation in a diseased artery, however, changed comparatively little as the pressure was equalized. Consequently, a diseased artery was easily differentiated from normal simply by observing radial normal strain and strain rate during the compressed phase of the examination. These very preliminary ex- and in-vivo results suggest that even small changes in arterial stiffness accompanying vascular disease may be sensitively monitored with elasticity imaging.

In addition to qualitative assessment of vascular compliance, the non-linear elastic modulus of the vascular wall can be quantitatively estimated using a simple reconstruction procedure. If surrounding tissue can be modeled as a continuous medium with elastic modulus $E_2$, the elastic modulus $E_1$ of the artery wall can be reconstructed using Equation (4). Within an offset proportional to $E_2$, it is possible to reconstruct the arterial elastic modulus as a function of mean arterial strain from the ratio $$\left[\frac{\Delta p}{\Delta \varepsilon}\right]$$

at the following different levels of sophistication:
- assume a fixed geometric scale factor $K_1$ for all subjects;
- automatically determine a and r from B-scan images using lumen boundary detection algorithms assuming a fixed wall thickness for all subjects to compute $K_1$;
- automatically determine a, b, and r from B-scan images to compute $K_1$.

This procedure overestimates the arterial elastic modulus by as much as $K_2 E_2$. This should not pose a practical problem at high preloads, but it could be a source of error at low preloads (i.e., pressure equalized) where $K_2 E_2$ may not be much smaller than $E_1$. The offset may only be a practical issue for low arterial moduli where it can limit the detection of subtle changes in arterial compliance such as in normal or near normal arteries.

Both ex- and in-vivo measurements presented herein, as well as a large body of previous literature, suggest that the non-linear change in arterial elastic modulus with preload can be modeled as an exponential function. Consequently, a simple linear least squares fit to the natural log of the estimated elastic modulus as a function of preload can fully characterize the vessel wall's non-linear mechanical properties. A major advantage of this fit procedure is that only a few points are needed over a limited range of preloads to estimate the elastic modulus of the undistended artery. This may be very valuable in applications such as assessment of carotid compliance where it may be difficult to equalize the pressure all the way to the diastolic limit. Again, the elastic properties of the background medium will influence the fit, but they should not significantly alter the results except in the small preload limit of highly compliant arteries. In any event, both the intercept (i.e., the elastic modulus of the undistended artery) and the non-linear parameter (i.e., the slope of the fit) can assess the vascular compliance. Because of the large non-linear parameter in arterial tissue compared to most soft tissues, the slope should not be greatly affected by the surrounding medium. This hypothesis, as well as the predictive value of each parameter, can be tested in controlled ex-vivo studies.

External force measurement provides additional information about the elastic modulus of the surrounding muscle to further refine the reconstruction procedure. A commercial blood pressure cuff has been modified to have an acoustic window through which an ultrasound scan can be performed. A monometer attached to the cuff monitors the external force (FIGS. 8a and 8b). Force is recorded and input to a modified reconstruction algorithm accounting for the finite elastic modulus of surrounding tissue. This procedure can also be tested in controlled ex-vivo studies.

Reconstruction procedures presented herein focus on the static elastic properties of the arterial wall. It is well known that the arterial wall is a viscoelastic medium (Hardung, 1962). Consequently, additional information can be obtained by comparing strain rate measurements with the arterial pressure pulse to derive time constants related to viscoelastic parameters.

Assessing arterial elasticity has many important clinical applications. This method allows localized assessment of vascular elasticity that may reflect the degree of both local and general vascular disease. It may be useful in pre-operative assessment for certain vascular surgery procedures, since the elastic properties of the vessel may reflect the capacity of the artery to remodel, influencing clinical outcomes. For example, in surgically creating an arterial-venous anastomosis in hemodialysis fistula creation, the artery dilates to create a manifold increase in volume flow through the fistula to accommodate hemodialysis (Konner et al., 2003). Inelastic, diseased arteries, so prevalent in end-stage renal disease, may greatly influence the outcome of the procedure (Konner et al., 2003). Assessing the elasticity of arteries preoperatively may favorably influence site selection, prevent the development of peripheral ischemia and improve clinical outcomes. The ease of collecting data reliably, such as with a modified blood pressure cuff (FIG. 8b), will be important in assessing the utility of this method in the clinical setting.

Appendix A

Figure 11:
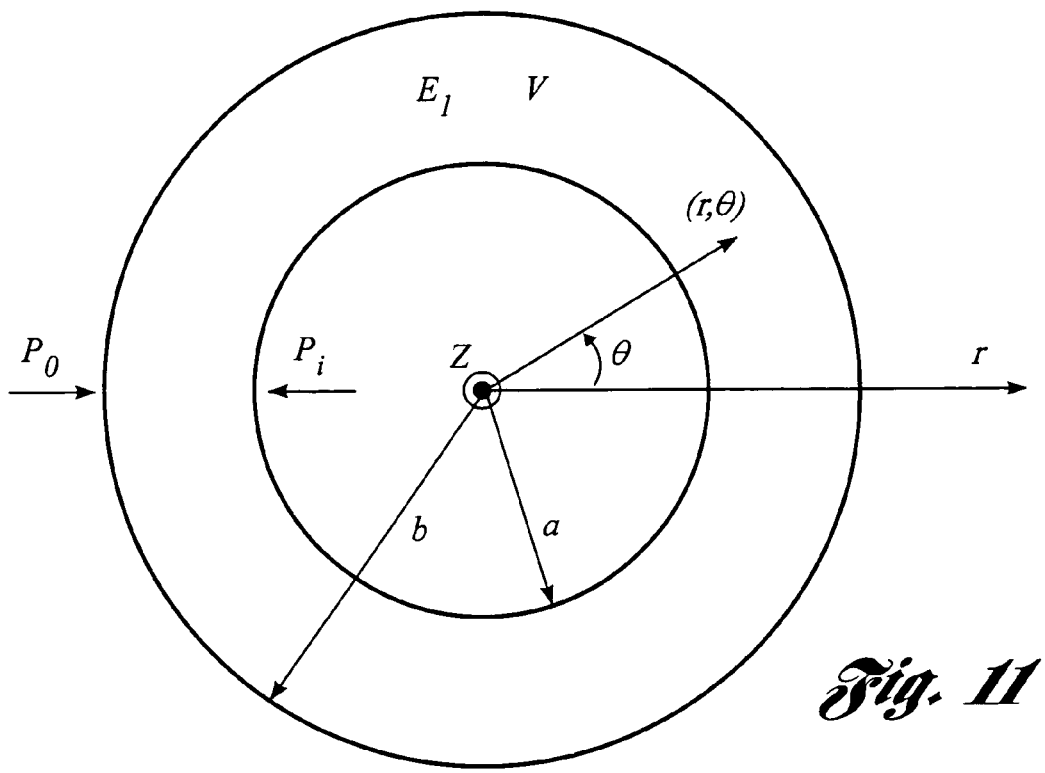
FIGS. 11 and 12 respectively relate internal and external arterial pressures and tissue elasticities to Young's modulus and arterial strain.

Referring now to FIG. 11, consider an elastic circular cylinder subject to hydrostatic pressure. The cylinder is long enough compared to its cross-sectional area to assume a plane strain state. Assuming isotropy in the axial direction and homogeneity in the radial direction, only normal stress exists. Considering axial symmetry, radial displacement depends only on the distance r from the center of the cylinder:

$$u_r(r) = -\frac{A}{r} + Br, \qquad \text{(A-1)}$$

where A and B are constants related to the material characteristics and geometry.

The corresponding radial and tangential strains are:

$$\varepsilon_r(r) = \frac{\partial u_r}{\partial r} = \frac{A}{r^2} + B, \qquad \text{(A-2)}$$

$$\varepsilon_\theta(r) = \frac{u_r}{r} = -\frac{A}{r^2} + B. \qquad \text{(A-3)}$$

Stress-strain relations for this problem are:

$$\varepsilon_r(r) = \frac{1}{E}[\sigma_r - \nu(\sigma_\theta + \sigma_z)] \qquad \text{(A-4)}$$

$$\varepsilon_\theta(r) = \frac{1}{E}[\sigma_\theta - \nu(\sigma_r + \sigma_z)] \qquad \text{(A-5)}$$

$$\varepsilon_z(r) = \frac{1}{E}[\sigma_z - \nu(\sigma_r + \sigma_\theta)], \qquad \text{(A-6)}$$

where $\sigma_i$ is the $i^{th}$ component of the stress tensor and $\nu$ is Poisson's ratio.

Since $\varepsilon_z = 0$ for a plane strain case, Equation (A-6) becomes:

$$\sigma_z = \nu(\sigma_r + \sigma_\theta). \qquad \text{(A-7)}$$

With this expression, Equations (A-5) and (A-6) can be rewritten as:

$$\varepsilon_r(r) = \frac{1}{E}(1+v)[(1-v)\sigma_r - v\sigma_\theta] \quad \text{(A-8)}$$

$$\varepsilon_\theta(r) = \frac{1}{E}(1+v)[(1-v)\sigma_\theta - v\sigma_r]. \quad \text{(A-9)}$$

Combining Equations (A-8) and (A-9) to eliminate $\sigma_\theta$ yields:

$$(1-v)\varepsilon_r + v\varepsilon_\theta = \frac{1}{E}(1+v)(1-2v)\sigma_r. \quad \text{(A-10)}$$

Substituting Equations (A-2) and (A-3) and applying boundary conditions at inner ($\sigma_r = -p_o$, at r=b, where $p_o$ is the external pressure) surfaces lead to:

$$(1-2v)\frac{A}{a^2} + B = \frac{-p_i}{E}(1+v)(1-2v) \quad \text{(A-11)}$$

$$(1-2v)\frac{A}{b^2} + B = \frac{-p_o}{E}(1+v)(1-2v). \quad \text{(A-12)}$$

Combining Equations (A-11) and (A-12) determines the unknown coefficients, A and B. The radial strain of interest herein can be expressed as:

$$\varepsilon_r = \frac{(p_o - p_i)a^2b^2(1-v)}{E(b^2-a^2)r^2} - \frac{(b^2 p_o - a^2 p_i)(1+v)(1-2v)}{E(b^2-a^2)}. \quad \text{(A-13)}$$

Assuming incompressibility, v=0.5, Equation (A-13) reduces to:

$$\varepsilon_r = \frac{3(p_o - p_i)a^2b^2}{2E(b^2-a^2)r^2} \quad a < r < b. \quad \text{(A-14)}$$

Appendix B

Figure 12:
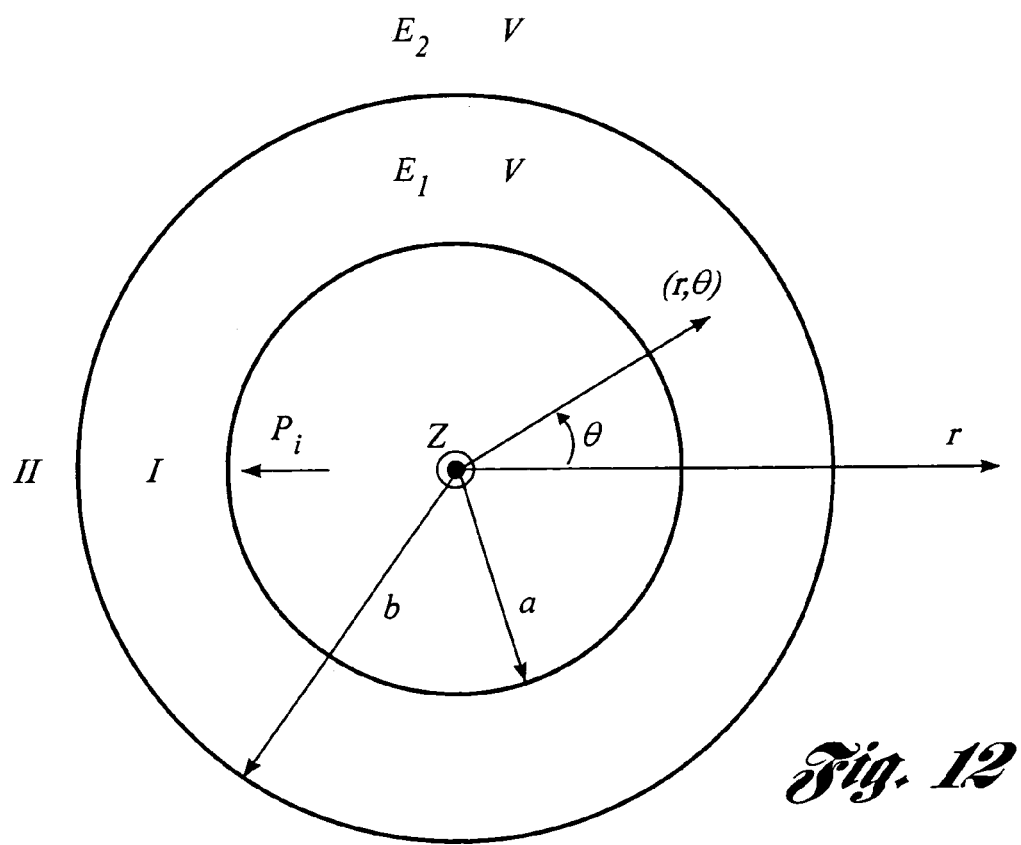

Referring now to FIG. 12, consider the same cylinder as in Appendix A surrounded by a homogeneous material which has different elastic modulus. Employing the same assumptions as in Appendix A, displacements and resulting strains in media I and II can be expressed as follows:

$$\text{I:} \quad u_{I,r}(r) = -\frac{A}{r} + Br \quad \text{(B-1)}$$

$$\varepsilon_{I,r}(r) = \frac{\partial u_r}{\partial r} = \frac{A}{r^2} + B \quad \text{(B-2)}$$

$$\varepsilon_{I,\theta}(r) = \frac{u_r}{r} = -\frac{A}{r^2} + B, \quad \text{(B-3)}$$

$$\text{II:} \quad u_{II,r}(r) = -\frac{C}{r} + Dr \quad \text{(B-4)}$$

$$\varepsilon_{II,r}(r) = \frac{\partial u_r}{\partial r} = \frac{C}{r^2} + D \quad \text{(B-5)}$$

-continued $$\varepsilon_{I,\theta}(r) = \frac{u_r}{r} = -\frac{C}{r^2} + D. \quad \text{(B-6)}$$

Note that D=0 to satisfy the boundary condition at infinity, i. e., no displacement. Using the same procedure as in Appendix A, radial stresses in medium I and II can be expressed as follows:

$$\text{I:} \quad \sigma_{I,r}(r) = \frac{E_1}{(1+v)(1-2v)}[(1-v)\varepsilon_{I,r} + v\varepsilon_{I,\theta}] \quad \text{(B-7)}$$

$$\text{II:} \quad \sigma_{II,r}(r) = \frac{E_2}{(1+v)(1-2v)}[(1-v)\varepsilon_{II,r} + v\varepsilon_{II,\theta}], \quad \text{(B-8)}$$

where $E_1$ is the arterial elastic modulus and $E_2$ is the modulus of the surrounding medium. Applying a boundary condition at the inner surface ($\sigma_{I,r} = -p_i$, at r=a), and two boundary conditions at the outer surface ($\sigma_{II,r} = -p_o$, $\sigma_{II,r} = \sigma_I$, r, at r=b) yields:

$$(1-2v)\frac{A}{a^2} + B = \frac{-p_i}{E_i}(1+v)(1-2v) \quad \text{(B-9)}$$

$$-\frac{A}{b} + bB = -\frac{C}{b} \quad \text{(B-10)}$$

$$\frac{(1-2v)E_2}{b^2}C = \frac{(1-2v)E_1}{b^2}A + E_1 B. \quad \text{(B-11)}$$

Combining Equations (B-9), (B-10), and (B-11) determines A, B, and C:

$$A = \frac{p_i(1+v)a^2b^2[E_1 + (1-2v)E_2]}{E_1\{(E_1-E_2)a^2 - [E_1 + (1-2v)E_2]b^2\}} \quad \text{(B-12)}$$

$$B = \frac{-p_i(1+v)(1-2v)a^2(E_1-E_2)}{E_1\{(E_1-E_2)a^2 - [E_1 + (1-2v)E_2]b^2\}} \quad \text{(B-13)}$$

$$C = \frac{2p_i(1+v)(1-v)a^2b^2 E_1}{E_1\{(E_1-E_2)a^2 - [E_1 + (1-2v)E_2]b^2\}}. \quad \text{(B-14)}$$

Assuming incompressibility, v=0.5, radial strain in medium I can be reduced to:

$$\varepsilon_{I,r}(r) = \frac{-3a^2b^2 p_i}{2(b^2-a^2)r^2} \bigg/ \left[E_1 + \frac{a^2}{(b^2-a^2)}E_2\right]. \quad \text{(B-15)}$$

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for measuring a mechanical property of a vascular wall which deforms in response to a transmural force under usual physiologic pressures, the method comprising:

altering an initial transmural force to obtain at least one altered transmural force wherein the step of altering includes the step of reducing the transmural force to obtain a reduced transmural force and wherein the step of reducing includes the step of applying an external pressure to the vascular wall;

measuring local changes in position of at least one location within the vascular wall resulting from physiologic pressures with the at least one altered transmural forces during the step of altering; and determining a value for the mechanical property based on a measured amount of the local changes.

2. The method as claimed in claim 1, wherein the mechanical property is a non-linear elastic property of the vascular wall.

3. The method as claimed in claim 1, wherein the step of measuring includes the step of non-invasively, ultrasonically imaging the vascular wall.

4. The method as claimed in claim 1, wherein the external pressure is substantially equal to a baseline internal pressure and wherein the vascular wall deforms by pulse pressure during a cardiac cycle.

5. The method as claimed in claim 1, wherein the step of reducing includes reducing an internal pressure to the vascular wall.

6. The method as claimed in claim 1, wherein the vascular wall deforms a relatively small amount in response to a transmural force under usual physiologic pressures and a relatively large amount in response to physiologic pressures with the altered transmural force.

7. The method as claimed in claim 1, wherein the step of determining includes the step of directly estimating strain of the vascular wall.

8. A method for measuring a mechanical property of a vascular wall, the vascular wall being characterized by a relationship of arterial pressure versus strain that exhibits a relatively large slope under physiologic pressure caused by an arterial pressure pulse having a first mean arterial pressure and that exhibits a relatively small slope under physiologic pressure caused by an arterial pressure pulse having a second mean arterial pressure, the method comprising:

altering the first mean arterial pressure to obtain the second mean arterial pressure;

measuring local changes in position of at least one location within the vascular wall at the second mean arterial pressure; and determining a valuefor the mechanical property based on the measured amount of the local changes.

9. The method as claimed in claim 8, wherein the step of measuring includes the step of non-invasively, ultrasonically imaging the vascular wall.

10. The method as claimed in claim 8, wherein the step of altering includes the step of reducing the first mean arterial pressure to obtain the second mean arterial pressure.

11. The method as claimed in claim 10, wherein the step of reducing includes the step of applying an external pressure to the vascular wall.

12. The method as claimed in claim 11, wherein the external pressure is substantially equal to a baseline internal pressure and wherein the vascular wall deforms by pulse pressure during a cardiac cycle.

13. The method as claimed in claim 10, wherein the step of reducing includes reducing an internal pressure to the vascular wall.

14. The method as claimed in claim 8, wherein the step of determining includes the step of directly estimating strain of the vascular wall.

15. A method for determining health of a vascular structure including a vascular wall which deforms in response to a transmural force under usual physiologic pressures, the method comprising:

altering an initial transmural force to obtain at least one altered transmural force wherein the step of altering includes the step of reducing the transmural force to obtain a reduced transmural force, wherein the step of reducing includes the step of applying an external pressure to the vascular wall;

measuring local changes in position of at least one location within the vascular wall resulting from physiologic pressures with the at least one altered transmural force during the step of altering; and determining the health of the vascular structure based on the measured amount of the local changes.

16. The method as claimed in claim 15, wherein the step of measuring includes the step of ultrasonically imaging the vascular wall.

17. The method as claimed in claim 15, wherein the external pressure is substantially equal to a baseline internal pressure and wherein the vascular wall deforms by pulse pressure during a cardiac cycle.

18. The method as claimed in claim 15, wherein the step of reducing includes reducing an internal pressure to the vascular wall.

19. The method as claimed in claim 15, wherein the vascular wall deforms a relatively small amount in response to a transmural force under usual physiologic pressures and a relatively large amount in response to physiologic pressures with the altered transmural force.

20. The method as claimed in claim 15, wherein the step of determining includes the step of directly estimating strain of the vascular wall.

21. A system for measuring a mechanical property of a vascular wall which deforms in response to a transmural force under usual physiologic pressures, the system comprising:

means for altering an initial transmural force to obtain at least one altered transmural force wherein the means for altering includes means for reducing the transmural force to obtain a reduced transmural force and wherein the means for reducing includes means for applying an external pressure to the vascular wall;

means for measuring local changes in position of at least one location within the vascular wall resulting from physiologic pressures with the altered transmural forces while the means for altering is altering the initial transmural force; and means for determining a value for the mechanical property based on the measured amount of the local changes.

22. The system as claimed in claim 21, wherein the mechanical property is a non-linear elastic property of the vascular wall.

23. The system as claimed in claim 21, wherein the means for measuring includes means for non-invasively, ultrasonically imaging the vascular wall.

24. The system as claimed in claim 21, wherein the external pressure is substantially equal to a baseline internal pressure and wherein the vascular wall deforms by pulse pressure during a cardiac cycle.

25. The system as claimed in claim 21, wherein the means for reducing includes means for reducing an internal pressure to the vascular wall.

26. The system as claimed in claim 21, wherein the vascular wall deforms a relatively small amount in response to a transmural force under usual physiologic pressures and a relatively large amount in response to physiologic pressures with the altered transmural force.

27. The system as claimed in claim 21, wherein the means for determining includes means for directly estimating strain of the vascular wall.

28. A system for measuring a mechanical property of a vascular wall, the vascular wall being characterized by a relationship of arterial pressure versus strain that exhibits a relatively large slope under physiologic pressure caused by an arterial pressure pulse having a first mean arterial pressure and that exhibits a relatively small slope under physiologic pressure caused by an arterial pressure pulse having a second mean arterial pressure, the system comprising:

means for altering the first mean arterial pressure to obtain the second mean arterial pressure;

means for measuring local changes in position of at least one location within the vascular wall at the second mean arterial pressure; and means for determining a value for the mechanical property based on the measured amount of the local changes.

29. The system as claimed in claim 28, wherein the means for measuring includes means for non-invasively, ultrasonically imaging the vascular wall.

30. The system as claimed in claim 28 wherein the means for altering includes means for reducing the first mean arterial pressure to obtain the second mean arterial pressure.

31. The system as claimed in claim 30, wherein the means for reducing includes means for applying an external pressure to the vascular wall.

32. The system as claimed in claim 31, wherein the external pressure is substantially equal to a baseline internal pressure and wherein the vascular wall deforms by pulse pressure during a cardiac cycle.

33. The system as claimed in claim 30, wherein the means for reducing includes the means for reducing an internal pressure to the vascular wall.

34. The system as claimed in claim 28, wherein the means for determining includes means for directly estimating strain of the vascular wall.

35. A system for determining health of a vascular structure including a vascular wall which deforms in response to a transmural force under usual physiologic pressures, the system comprising:

means for altering an initial transmural force to obtain at least one altered transmural force wherein the means of altering includes means for reducing the transmural force to obtain a reduced transmural force and wherein the means for reducing includes means for applying an external pressure to the vascular wall;

means for measuring local changes in position of at least one location within the vascular wall resulting from physiologic pressures with the altered transmural forces while the means for altering is altering the initial transmural force; and means for determining the health of the vascular structure based on the measured amount of the local changes.

36. The system as claimed in claim 35, wherein the means for measuring includes means for non-invasively, ultrasonically imaging the vascular wall.

37. The system as claimed in claim 35, wherein the external pressure is substantially equal to a baseline internal pressure and wherein the vascular wall deforms by pulse pressure during a cardiac cycle.

38. The system as claimed in claim 35, wherein the means for reducing includes means for reducing an internal pressure to the vascular wall.

39. The system as claimed in claim 35, wherein the vascular wall deforms a relatively small amount in response to a transmural force under usual physiologic pressures and a relatively large amount in response to physiologic pressures with the altered transmural force.

40. The system as claimed in claim 35, wherein the means for determining includes means for directly estimating strain of the vascular wall.

* * * * *